United States Patent [19]

Reinalda et al.

[11] Patent Number: 5,021,387
[45] Date of Patent: Jun. 4, 1991

[54] CATALYST FOR THE PREPARATION OF HYDROCARBONS FROM CARBON MONOXIDE AND HYDROGEN

[75] Inventors: Donald Reinalda, Amsterdam; Jelte Kars, Rotterdam/Pernis, both of Netherlands

[73] Assignee: Shell Oil Company, Houston, Tex.

[21] Appl. No.: 535,694

[22] Filed: Jun. 11, 1990

[30] Foreign Application Priority Data

Aug. 18, 1989 [GB] United Kingdom ............... 8918845

[51] Int. Cl.$^5$ .................... B01J 21/08; B01J 23/74
[52] U.S. Cl. .................... 502/260; 518/715
[58] Field of Search .................... 502/260, 325, 332

[56] References Cited

U.S. PATENT DOCUMENTS

| | | | |
|---|---|---|---|
| 3,909,455 | 9/1975 | Rainer et al. | 502/332 X |
| 4,542,122 | 9/1985 | Payne et al. | 502/325 |
| 4,637,993 | 1/1987 | Van Erp et al. | 502/242 |
| 4,738,948 | 4/1988 | Iglesia et al. | 502/326 |

FOREIGN PATENT DOCUMENTS 0127220 12/1984 European Pat. Off. .

Primary Examiner—W. J. Shine

[57] ABSTRACT

The invention relates to a process for the preparation of a catalyst suitable for the preparation of hydrocarbons from carbon monoxide and hydrogen, wherein a cobalt compound is applied on a porous, inert carrier and the carrier is dried and calcined forming the catalyst, characterized in that the cobalt compound is cobalt nitrate, and the carrier provided with the cobalt compound is calcined in an atmosphere containing nitrogen oxide at a concentration of at least 20% by volume, not taking the water content of the atmosphere into consideration, and to a catalyst comprising agglomerates of cobalt oxide crystallites distributed over a porous, inert carrier, having an agglomerate size of about 1-10 micrometer.

3 Claims, No Drawings 5,021,387

CATALYST FOR THE PREPARATION OF HYDROCARBONS FROM CARBON MONOXIDE AND HYDROGEN

FIELD OF INVENTION

The present invention relates to a process for the preparation of a catalyst suitable for the preparation of hydrocarbons from a mixture of carbon monoxide and hydrogen, and to said catalyst per se.

BACKGROUND OF INVENTION

The preparation of hydrocarbons from a mixture comprising carbon monoxide and hydrogen, by contacting this mixture at elevated temperatures and pressure with a suitable catalyst, is known in the literature as the Fischer-Tropsch process. Suitable catalysts for this synthesis reaction are amongst others catalysts comprising cobalt supported on a porous, inert carrier. Optionally a noble metal, e.g. ruthenium, may be added. Furthermore, the catalysts preferably contain at least one other metal from Group IVb and/or VIb, most preferably chosen from the group consisting of hafnium, zirconium, titanium and chromium. Magnesium, thorium and manganese may also be used. The catalysts preferably contain about 3-80 parts by wt cobalt, especially 15-50 parts by weight of cobalt, optionally 0.05-0.5 parts by wt ruthenium, and about 0.1-100 parts by wt of other metal (as per 100 parts by wt carrier), preferably 5-40 parts of zirconium. The porous carrier is preferably a refractory oxide carrier, such as silica, alumina, zirconia, titania and mixtures thereof; preferably silica is used. Impregnation and/or kneading are conventional methods for the incorporation of cobalt and optionally the promotor and other metals into the carrier. For further information reference is made to EP-A-127,220.

The metal loaded carrier is dried in order to remove the solvent at temperatures varying from ambient temperature to 200° C. at normal pressure. Thereafter the dried catalyst composition is calcined at temperatures from 200°-700° C., preferably 300°-600° C., in order to remove crystal water and to decompose organic and inorganic compounds to oxides and volatile decomposition products, for instance nitrogen oxide.

The catalysts are preferably used in the form of spherical, cylindrical or lobed particles having a nominal diameter of 0.5-5 mm, preferably 1-2 mm. The carrier particles may be prepared by any conventional method, such as compression, granulation, (hot)pressing or extrusion of powderous carrier material, optionally using a binder material. Carrier spheres, in particular silica containing spheres, are suitably prepared by means of the "oil-drop" method, wherein spheres are formed from drops of silica precursor and an acid solidifying when falling in an oil bath, or by means of the "sol-gel" method. Alumina based carriers are preferably made by extrusion or by the above described "oil-drop" method.

Prior to the use of the above-described Fischer-Tropsch catalysts, the catalysts have to be activated. This activation is suitably carried out by contacting the catalyst at a temperature between 100° and 600° C., preferably between 200° and 350° C., with hydrogen or a hydrogen containing gas.

DETAILED DESCRIPTION OF THE INVENTION

The preparation of hydrocarbons from a mixture of carbon monoxide and hydrogen, using the catalyst according to the invention is preferably carried out at a temperature of 100°-500° C., at a total pressure of 1-200 bar absolute and a space velocity of 200-20,000 $m^3$ (STP) gaseous feed/$m^3$ reaction zone/hour. Preferred process conditions for the preparation of hydrocarbons include a temperature from 150°-300° C., more preferably 180°-230° C., a pressure of 5-100 bar absolute, more preferably 15-30 bar, and a space velocity of 500-5,000 $m^3$ (STP) gaseous feed/$m^3$ reaction zone/hour. The term "STP" used herein means standard temperature (of 0° C.) and pressure (1 bar absolute). The gaseous feed preferably has a hydrogen/carbon monoxide ratio of 0.4-4, more preferably 0.8-2.5, still more preferably 1.0-1.5.

Further research on the activity and selectivity, especially the $C_{5+}$ selectivity, of the catalysts revealed that the selectivity and the activity may be further improved, if during the calcination the metal loaded carrier resides in an atmosphere containing nitrogen oxide.

The present invention, therefore, relates to a process for the preparation of a catalyst suitable for the preparation of hydrocarbons from a mixture of carbon monoxide and hydrogen, wherein a cobalt compound is applied on a porous, inert carrier and the carrier provided with the cobalt compound is dried and calcined forming the catalyst, characterized in that the cobalt compound is cobalt nitrate, and the carrier provided with the cobalt compound is calcined in an atmosphere containing nitrogen oxide in a concentration of at least 20% by volume, not taking the water content of the atmosphere into consideration.

Preferably the nitrogen oxide originates from the decomposition of cobalt nitrate, and this decomposition gas is present during calcination in the calcination furnace, the atmosphere of which is not purged at all, or is purged at a low velocity.

The concentration of the nitrogen oxide during the calcination process is suitably between 25 and 100% by volume, preferably between 40 and 95% by volume, more preferably between 60 and 90% by volume, not taking the water content of the atmosphere into consideration. The concentration of the nitrogen oxide during calcination may be established by measuring the nitrogen oxide concentration in the (dried) off-gas from the calcination process or by taking samples out of the calcination bed.

The calcination in the presence of nitrogen oxide results in the formation of relatively large agglomerates of cobalt oxide crystallites after reduction. The relatively large cobalt oxide agglomerates usually have a size of between 1 and 10 micrometer, preferably between 1 and 5 micrometer, more preferably between 1 and 3 micrometer, still more preferably between 1.5 and 2.5 micrometer. Therefore, the invention also relates to a process for the preparation of catalysts suitable for the preparation of hydrocarbons as described hereinbefore, wherein the nitrogen oxide concentration is such that cobalt oxide containing agglomerates are formed having a size of about 1-10 micrometer, preferably between 1-5 micrometer, more preferably between 1-3 micrometer, still more preferably between 1.5-2.5 micrometer, as well as to catalysts having cobalt agglomerates having a size of about 1-10 micrometer, preferably between 1-5 micrometer, more preferably between 1-3 micrometer, still more preferably between 1.5-2.5 micrometer.

The invention further relates to a process for the preparation of hydrocarbons by catalytic reaction of carbon monoxide and hydrogen comprising the use of a catalyst as described hereinbefore.

The invention will be illustrated hereafter by a practical example of the preparative process of the catalyst and of the process for the preparation of hydrocarbons using this catalyst.

EXAMPLE 1

On the surface of a silica carrier particles zirconia are deposited. Then the zirconia impregnated carrier particles are impregnated with an aqueous solution of cobalt nitrate. The dried particles are divided into two portions (A and B). Sample A is dried in a laboratory rotating film evaporator, wherein heat of vaporation is supplied by an oil bath (200° C.) and transferred via the wall of the rotating flask to the impregnated particles (simulating a rotary kiln drier). Air (25° C.) is used as a purge stream to remove the vapors.

Sample B is dried using hot gas in a vibrating bed configuration wherein heat of vaporation is supplied by the gas (25° C., simulating a belt drier).

Each catalyst sample (A and B) is divided in two equal parts. The first part (A-S and B-S) are calcined during 1 hour at 500° C. in a stationary oven.

The second part of the dried samples (A-T and B-T) are calcined in a standard fixed bed configuration using an air stream (GHSV of 500 Nl/(l.h), resulting in a low nitrogen oxide ($NO_x$) partial pressure in the catalyst bed to be calcined. The nitrogen oxide partial pressure under these conditions is lower than 2% by volume.

EXAMPLE 2

The four catalyst samples (A-S, B-S, A-T and B-T) are tested for their catalytic activity in the preparation of hydrocarbons from a mixture of carbon monoxide and hydrogen.

Each catalyst sample (comprising 34 pbw $Co_3O_4$, 16 pbw $ZrO_2$, and 100 pbw $SiO_2$) is reduced (260° C., 3 bar (absolute), 6,000 GHSV), in a gas stream with an increasing hydrogen concentration (1-100%).

The test conditions are as follows: pressure 21 bar (absolute), 800 GHSV, hydrogen/carbon monoxide ratio in the feet equal to 2.

The results are shown in the following table:

| Catalyst | A-S | B-S | A-T | B-T |
|---|---|---|---|---|
| Performance | at run hour 200 | | | |
| Temperature, °C. | 195 | 195 | 205 | 205 |
| STY, $gC_{1+}$, $l^{-1}$, $h^{-1}$ | 100 | 100 | 100 | 100 |
| $C_{5+}$ selectivity, % w on $C_{1+}$ | 76/79 | 75 | 75 | 76 |

From this table it is apparent that at the same standard yield, adjusted to 100 $gC_{1+}$, $l^{-1}$, $h^{-1}$, with the catalysts calcined according to the invention, comprising the agglomerates of cobalt crystallites, the same yield can be obtained at lower temperatures. At these lower temperatures the occurrence of side reactions is much lower, whereas less iso-hydrocarbons are formed.

What I claim as my invention is:

1. Catalyst comprising agglomerates of cobalt oxide crystallites distributed over a porous, inert carrier, having an agglomerate size of about 1-10 micrometers, wherein the carrier is silica.

2. The catalyst as claimed in claim 1, wherein said cobalt oxide crystallites have an agglomerate size of about 1-3 micrometer.

3. The catalyst as claimed in claim 1, wherein said cobalt oxide crystallites have an agglomerate size of about 1.5-2.5 micrometer.

* * * * *